(12) United States Patent
Dobetti et al.

(10) Patent No.: US 7,793,871 B2
(45) Date of Patent: Sep. 14, 2010

(54) DRUG ACTIVATION PROCESS AND VIBRATIONAL MILL THEREFOR

(75) Inventors: Luca Dobetti, Trieste (IT); Leonardo Rabaglia, Parma (IT); Massimo Bresciani, Trieste (IT)

(73) Assignee: Eurand Pharmaceuticals Ltd., Dublin (IE)

( * ) Notice: Subject to any disclaimer, the term of this patent is extended or adjusted under 35 U.S.C. 154(b) by 0 days.

(21) Appl. No.: 12/146,297

(22) Filed: Jun. 25, 2008

(65) Prior Publication Data

US 2008/0251615 A1 Oct. 16, 2008

Related U.S. Application Data

(62) Division of application No. 10/481,377, filed as application No. PCT/EP02/06050 on Jun. 3, 2002, now abandoned.

(30) Foreign Application Priority Data

Jun. 29, 2001  (IE) ................................. 2001/0620

(51) Int. Cl.
    *B02C 17/00* (2006.01)
(52) U.S. Cl. ............................. 241/26; 241/27; 241/175
(58) Field of Classification Search .................. 241/26, 241/27, 175
See application file for complete search history.

(56) References Cited

U.S. PATENT DOCUMENTS

| | | | | |
|---|---|---|---|---|
| 3,630,774 A | * | 12/1971 | Knight | 127/32 |
| 3,744,726 A | * | 7/1973 | Groszek | 241/30 |
| 4,076,935 A | * | 2/1978 | Eichenseer et al. | 536/86 |
| 4,253,839 A | * | 3/1981 | Spietschka et al. | 8/565 |
| 5,202,129 A | * | 4/1993 | Samejima et al. | 424/489 |
| 5,275,824 A | * | 1/1994 | Carli et al. | 424/490 |
| 5,738,865 A | * | 4/1998 | Baichwal et al. | 424/440 |
| 5,954,565 A | | 9/1999 | Mori | |

FOREIGN PATENT DOCUMENTS

| | | |
|---|---|---|
| DE | 4343742 A1 | 6/1995 |
| WO | 9632931 A2 | 10/1996 |

OTHER PUBLICATIONS

"Installation, Operation & Maintenance Specifications for DM28L: Food Grade Vibro-Energy Grinding Mill for Vectorpharma Int'l. SpA, Sales Order # 655391-01 & 655391-02,", SWECO®, Apr. 1997.

Kawano, K., and H. Ogino, "Physicochemical Properties of Ground Mixtures of Crystalline Medicinals With Microcrystalline Cellulose or Cyclodextrins," Journal of Pharmacobio-Dynamics 5(1):s-4, Jan. 1982.

Nakai, Y., et al., "Effects of Grinding on Physical and Chemical Properties of Crystalline Medicinals With Microcrystalline Cellulose. I. Some Physical Properties of Crystalline Medicinals in Ground Mixtures," Chemical and Pharmaceutical Bulletin (Tokyo) 25(12):3340-3346, Dec. 1977.

SWECO®, Vibration Mill Marketing Literature, <http:\www.sweco.com>[retrieved Nov. 26, 2006], 4 pages.

* cited by examiner

*Primary Examiner*—Bena Miller
(74) *Attorney, Agent, or Firm*—Christensen O'Connor Johnson Kindness PLLC

(57) ABSTRACT

The invention comprises a process for activating drugs by means of high-energy co-grinding of the drug with a pharmaceutical carrier, characterized by the use of a vibrational mill equipped with means that regulate the vibration frequency. The process, performed by modifying the frequency of vibration and keeping its amplitude constant, produces drug/carrier composites with a constant particle size in which the degree of drug activation increases in proportion to the frequency applied. The invention also includes a vibrational mill suitably modified to perform the process described.

12 Claims, No Drawings

DRUG ACTIVATION PROCESS AND VIBRATIONAL MILL THEREFOR

This application is a division of co-pending U.S. patent application Ser. No. 10/481,377 (now abandoned), filed Dec. 18, 2003, which is a §371 National Stage filing of International Application No. PCT/EP02/06050, filed Jun. 3, 2002, which claims priority from Ireland Application No. 2001/0620, filed Jun. 29, 2001. Each application is expressly incorporated herein by reference in its entirety.

FIELD OF INVENTION

This invention relates to the field of drug activation by high-energy co-grinding. It comprises a process that produces pharmaceutical composites with controlled activation and particle size. It also comprises a vibrational mill specifically adapted for the performance of this process.

PRIOR ART

The formulation and administration of drugs which are slightly soluble or insoluble is one of the major problems that arises in pharmaceutical research. Slightly soluble or insoluble drugs often present insufficient absorption in the gastrointestinal tract, and consequently a low level of bioavailability. As a result, pharmaceutical formulations must contain large amounts of such drugs, and need to be administered repeatedly during the day, in order to maintain a plasma concentration with therapeutic efficacy.

The factors that influence the solubility and dissolution rate of molecules in water are associated with their chemical-physical properties such as crystalline form, particle size, surface area and wettability. If these parameters are suitably modified, the chemical-physical properties can be modified to aid the solubility of the molecule in water.

The mechanical/chemical activation by high-energy co-grinding of crystalline drugs with inert substances (carriers) is a technique that allows modification of the chemical-physical properties of drugs and consequently improves their solubility in water.

In particular, high-energy co-grinding:

enables the drug to be thermodynamically activated by destructuring of the crystal and forming an amorphous phase and/or nanocrystalline structures inside the carrier (Nakai et al. *Chem. Pharm. Bull.* 25, 3340, 1977; Kawano et al. *J. Pharm. Dyn.* 5, S4, 1982), this process being defined as "activation" of the drug for the sake of brevity;

reduces the size of the carrier particles containing the active constituent, thereby contributing to increase the dissolution rate of the drug.

The vibrational mill is one of the types of equipment most often used for high-energy co-grinding. The mill usually consists of a cylindrical chamber or reactor clad with inert material, inside which high-density grinding means are installed. The grinding means are bodies with a given shape, weight, volume and surface area, present inside the reactor in varying numbers but not attached to it; they are consequently free to move in response to mechanical stresses imparted outside the reactor by a vibrating mechanism. The grinding means are usually cylindrical bodies with flat or curved (dome-shaped) bases, made of high-density shockproof material, typically metal or metal oxide, such as aluminium oxide, zirconium oxide or steel.

To perform grinding, the mill is loaded with a preset quantity of grinding means and grinding powder, and made to vibrate. Grinding takes place by compression of the powder between the surfaces of the various grinding means which undergo free rotatory/vibratory movement.

The vibration mechanism is produced by an electric motor fitted to the reactor, to which two eccentric counterweights are attached in such a way that they can be regulated; the stresses imparted to the reactor cause a rotary/vibratory movement of the grinding means. The transfer of energy from the motor to the grinding chamber therefore depends on the power of the motor and on the weights and reciprocal positions of the two counterweights, which determine the amplitude of vibration of the chamber. The mills are constructed so as to vary the weight and reciprocal positions of the counterweights (also called guide angles) and thus modify the amplitude of vibration; the power of the motor is fixed and constant (DM28L Food Grade Vibro-Energy Mill. Sweco Manual).

The grinding process presents a considerable ability to activate drugs as a result of its ability to incorporate the drug into the carrier in the nanocrystalline or amorphous state (the states with the greatest solubility and bioavailability), and at the same time to reduce the size of the particles of drug/carrier composite. However, the conventional co-grinding process simultaneously leads to a reduction in the particle size of the drug/carrier composite, and at the same time to an increase in the level of activation of the drug. As a result, such a process can generally produce drug/carrier composites with a high level of activation and very fine particle size, but does not allow highly activated composites with a medium or coarse particle size, for example, to be produced. Nevertheless in some cases it is desirable to obtain a highly activated drug while avoiding extensive reduction of the final particle size of the drug-carries composite; this is because excessively fine granulation can make it difficult to process the substance when pharmaceutical formulations are prepared. In other cases, when the maximum thermodynamic activation (activation plateau) has been reached, it may be desirable to further reduce the particle size of the composite without prejudicing the intactness of the product (increase in mill temperature and degradation of drug and/or carrier). These effects and products cannot be obtained with the conventional co-grinding process in view of the process characteristics analysed above. There is consequently an unmet need for more selective co-grinding processes, capable to produce pharmaceutical composites with a controlled particle size and degree of activation of the drug, and in particular to control these two parameters independently.

SUMMARY

This invention is based on the finding that if, in a co-grinding process, the vibration frequency imposed on the mill (number of oscillations in time) is modified without varying the amplitude of the vibration (extension of oscillation), the degree of activation of the drug increases in proportion to the frequency imposed, while the particle size of the end product of co-grinding (drug/carrier composite) remains substantially unchanged.

The imposition of different vibration frequencies with the same amplitude enables the drug particle size to be reduced without reducing that of the final co-ground composite; it is therefore now possible to obtain a far wider range of combinations of degree of activation and particle size of the composite than was possible with conventional co-grinding.

The present invention relates to a process able to produce pharmaceutical composites with controlled activation and particle size, and a vibrational mill specifically adapted for the performance of this process.

DESCRIPTION OF INVENTION

The subject of this invention is a process for activating a drug by co-grinding of said drug with a pharmaceutical carrier, said process being characterised in that:
- co-grinding is performed in a vibrational mill equipped with means for regulating the vibration frequency
- the desired degree of activation is obtained by varying the vibration frequency, while the vibration amplitude is kept constant.

In this process, the degree of activation attained by the co-ground drug increases in proportion to the vibration frequency applied, while the particle size of the carrier-drug composite obtained remains constant. Thus by adjusting the frequency and keeping the amplitude constant, it is now possible to control the degree of activation of the drug reliably, without affecting the particle size of the end product of co-grinding.

For the purpose of this invention, "drug activation" means the ability to reduce or eliminate the amount of drug present in crystalline form by increasing its nanocrystalline and/or amorphous fraction.

The working value of the amplitude of vibration is preferably between 3 mm and 15 mm of shift, most preferably between 5 mm and 12 mm, measured on the axis perpendicular to the ground. Small changes of the vibration amplitude (i.e. +/−10%) do not interfere with obtaining the results of the present invention.

Once the amplitude value has been set, various drug/carrier composites with increasing degree of activation can be obtained by increasing the vibration frequency; these increases in frequency generate an increase in drug activation, while the particle size of the final drug/carrier composite remains constant. The vibration frequency is generated by and equal to the mill motor rotation frequency or rate. By way of example but not of limitation, the working frequency is generally between 200 and 4500 rpm, preferably between 500 and 4000 rpm, most preferably between 700 and 3500 rpm; the choice of specific working value depends on the degree of activation required: the higher the frequency, the greater the degree of activation.

The vibration amplitude can be set with known systems, for example with suitable counterweights positioned in such a way as to determine the amplitude of vibration of the grinding chamber. The operating frequency is set by regulating the motor rotation speed.

In the process to which this invention relates, the operator acts in the opposite way to that known according to the prior art. In conventional mills, the ideal activation conditions are sought by regulating the position of the counterweights (search for ideal vibration amplitude) with a fixed vibration frequency, determined by the power of the motor, whereas in the process in accordance with the invention, this research is performed at a constant amplitude, by varying the frequency (rotation speed) of the motor (search for ideal vibration frequency).

The process is performed by loading the mill with a suitable amount of drug and carrier, optionally pre-mixed; preferably the drug and carrier are introduced into the mill as two separate powders. By way of example, proportions of the drug and carrier of between 12:1 and 0.5:1 by weight, preferably between 5:1 and 1:1, can be used. The grinding time is usually between 1 and 8 hours; for each drug/carrier mixture a peak time (plateau) is present, after which grinding is complete and activation will not increase any further.

The carrier can be any solid pharmaceutical excipient, such as cross-linked and non-cross-linked polymers; examples of these products are: cross-linked polyvinylpyrrolidone (PVP-CL), cross-linked carboxymethyl cellulose (croscarmellose), polacrilin potassium, starch and its derivatives such as sodium starch glycolate (SSG), cyclodextrin (in particular β-cyclodextrin), cellulose and its derivatives; non-polymeric carriers such as silica and alumina can also be used. To ensure a higher level of activation, cross-linked polymers are preferably used.

The present process can be performed with any solid drug. The process of the invention is particularly advantageous for drugs which are slightly soluble or insoluble in water, because the phenomenon of activation is observed to the greatest extent in these products. Drugs with particularly low solubility are defined as "class II" and "class IV" drugs according to "*FDA/CDER Guidance for Industry. Waiver of in-vivo bioavailability and bioequivalence studies for immediate-release solid* oral dosage forms based on a Biopharmaceutical Classification System. August 2000". By way of example but not of limitation, these products include cox-2 inhibitors, antiinflammatory drugs such as nimesulide, piroxicam, naproxene, ketoprofen, ibuprofen and diacerheine, antifungal drugs such as griseofulvin, itraconazole, fluconazole, miconazole and ketonazole, bronchodilators/anti-asthmatic drugs such as zafrilukast, salbutamol, beclomethasone, flunisolide, clenbuterol, salmeterol and budesonide, steroids such as estradiol, estriol, progesterone, megestrol acetate, medroxyprogesterone acetate, antihypertensive/antithrombotic/vasodilator drugs such as nefedipine, nicergoline, nicardipine, lisinopril, enalapril, nicorandil, celiprolol and verapamil, benzodiazepines such as temazepam, diazepam, lorazepam, fluidiazepam, medazepam and oxazolam, anti-migraine drugs such as zolmitriptan and sumatriptan, antilipoproteinemic drugs such as fenofibrate, lovastatin, atorvastatin, fluvastatin, and simvastatin, anti-viral/antibactetial drugs such as tosufloxacin, ciprofloxacin, ritonavir, saquinavir, nelfinavir, acyclovir and indinavir, immunodepressant drugs such as tacrolimus, rapamycine and didanisine, anti-histaminic drugs such as loratadine, antitumour drugs such as etoposide, bicalutamide, tamoxifen, doclitaxel and paclitaxel, anti-psychotic drugs such as risperidone, anti-osteoporotic drugs such as raloxifene, anti-convulsant drugs such as carbamazepin and phenytoin, analgetic/narcotic drugs such as oxycodone, hydrocodone, morphine and butorpanol, muscle relaxant such as tinazadine, anti-ulcerative drugs such as famotidine. For the purpose of the invention, the term "drug" includes any active constituent with biological effects on man and/or animals; this term also includes mixtures of two or more drugs.

For the performance of the present process, the Applicant has developed and used a new mill which includes systems designed to regulate the vibration frequency. This modified mill constitutes part of the present invention. The system which regulates the vibration frequency is generally constituted by a potentiometer (or inverter) connected to the mill motor and suitably regulable by an operator; via regulation of the motor rotation speed, the potentiometer determines the vibration frequency imposed on the chamber, and therefore the vibratory energy of the grinding means. At the same time the oscillation capacity of the mil remains fixed within the amplitude range originally set.

Substantially any commonly available potentiometer can be used in the vibrational mill, provided that it is compatible with the voltage and current intensity of the mill in question. In general, it is useful for the potentiometer (inverter) to allow the mill motor to rotate at a speed (vibration frequency) of between 200 and 4500 rpm, preferably between 500 and 4000 rpm, most preferably between 700 and 3500 rpm.

The type of grinding means contained in the mill is not crucial to the invention, and reference should be made to the means commonly used in high-energy co-grinding as regards this aspect. They are normally bodies with a cylindrical or cylindroid shape, preferably with flat or convex bases. The dimensions of the grinding means are proportional to the volume of the mill. By way of example, means could be used in which the diameter and height are between 0.4 and 3 cm, independently of one another, and preferably between 0.6 and 1.3 cm. The grinding means are made of high-density shock-proof material (preferably with a density greater than 3 g/cc), such as aluminium oxide, zirconium oxide or steel. The grinding means are introduced into the mill in the quantities normally used for this type of equipment; by way of example, the grinding means occupy 20% to 90% of the total internal volume of the grinding chamber. The mill forming the subject of the invention is of pharmaceutical grade, namely a mill with a steel grinding chamber and linings made of plastic materials approved for pharmaceutical and/or food uses.

The process described here above can produce a variety of drug/carrier composites with constant particle size and different degrees of drug activation. This constitutes an evident advantage, for example when the particle size must not be too fine in order to avoid processing problems at subsequent stages, but a high level of drug activation is desired. The variable-frequency process enables the ideal ratio of the drug to be prepared in the amorphous, nanocrystalline or crystalline phase, without modifying the ideal particle size reduction kinetics, which could adversely affect the co-grinding process (e.g. temperature increase) and/or the subsequent processing stages (e.g. excessively fine particle size and problems of powder flow). Regulation of grinding with the potentiometer has the further advantage that it does not require any blockage of the apparatus, and can consequently be performed continuously during the process. This is impossible with conventional mills, in which the modification (moving the counterweights) requires interruption of the vibration and stoppage of the process, involving the risk of uneven grinding.

This invention will now be illustrated by reference to the following examples, which are given by way of example but not of limitation.

EXPERIMENTAL PART

Methods

The percentage of the drug in the amorphous, nanocrystalline or crystalline state was determined by differential scanning calorimetry using a Perkin-Elmer DSC7 calorimeter. The percentage of drug in the crystalline or nanocrystalline form is determined by comparing the fusion enthalpies relating to the crystalline form (at temperature Tm) and nanocrystalline form (at temperature T<Tm) with the enthalpy of the totally crystalline drug (100% crystallinity).

The titre of the drug included in the carrier is determined by spectrophotometry (UV/visible spectrum) or HPLC.

The particle size of the activated carrier/drug composite is expressed as the Specific Surface Area (SSA). The SSA is determined by helium absorption (BET).

The standard deviation of the percentage of amorphous, nanocrystalline and crystalline phase is 2%. The standard deviation of the SSA values is 0.5 m$^2$/g.

EXAMPLE 1

600 g of nimesulide and 1800 g of β-cyclodextrin are placed in a Sweco DM3 vibrational mill together with 80 kg of aluminium oxide grinding means. The co-grinding process is performed at a vibration amplitude of 10 mm, measured on the vertical axis, and at a vibration frequency of 1500 rpm (frequency of motor).

EXAMPLE 2

600 g of nimesulide and 1800 g of B-cyclodextrin are placed in a Sweco DM3 vibrational mill together with 80 kg of aluminium oxide grinding means. The co-grinding process is performed at a vibration amplitude of 10 mm, measured on the vertical axis, and at a vibration frequency of 500 rpm (frequency of motor).

EXAMPLE 3

600 g of nimesulide and 1800 g of β-cyclodextrin are placed in a Sweco DM3 vibrational mill together with 80 kg of aluminium oxide grinding means. The co-grinding process is performed at a vibration amplitude of 10 mm, measured on the vertical axis, and at a vibration frequency of 3500 rpm (frequency of motor).

The results of examples 1-3 are set out in Table 1.

TABLE 1

| | Kinetics of thermodynamic activation and increase in Specific Surface Area (reduction in particle size) | | | | | | | | | | | |
|---|---|---|---|---|---|---|---|---|---|---|---|---|
| Process | Example 1 | | | | Example 2 | | | | Example 3 | | | |
| time (hours) | Amorph. (%) | Nanocr. (%) | Crystal | SSA (m2g) | Amorph. (%) | Nanocr. (%) | Crystal | SSA (m2g) | Amorph. (%) | Nanocr. (%) | Crystal | SSA (m2g) |
| 0 | 0 | 0 | 100 | 4.5 | 0 | 0 | 100 | 4.5 | 0 | 0 | 0 | 4.5 |
| 1 | 21 | 16 | 63 | 7.6 | 9 | 12 | 79 | 7.9 | 28 | 21 | 51 | 7.7 |
| 2 | 28 | 32 | 40 | 7.4 | 14 | 23 | 63 | 7.6 | 37 | 40 | 13 | 7.5 |
| 3 | 33 | 52 | 15 | 6.8 | 18 | 33 | 49 | 7.4 | 44 | 51 | 5 | 7.2 |
| 4 | 40 | 52 | 8 | 7.3 | 23 | 38 | 39 | 7.4 | 47 | 51 | 2 | 7.3 |

The data set out in Table 1 show different thermodynamic activation kinetics at different vibration frequencies, while the particle size reduction kinetics (increase in SSA) remain substantially unchanged.

In particular, in the three examples, the SSA of the product remains substantially constant, regardless of the frequency values applied and the co-grinding time. Conversely, drug activation (% of amorphous and nanocrystalline phase) increases in proportion to the grinding frequency.

The invention claimed is:

1. A method for activating a drug in pharmaceutical composites having particles of constant size, comprising subjecting a drug and a pharmaceutical carrier to co-grinding in a vibrational mill equipped with means to regulate vibration frequency while vibration amplitude is kept constant, wherein drug activation degree increases in proportion to the vibration frequency applied while particle size remains constant.

2. The method of claim 1 wherein said vibrational mill includes a motor and said vibration frequency is varied by varying a rotational speed of said motor.

3. The method of claim 2 wherein said rotational speed is between 200 and 4500 rpm.

4. The method of claim 2 wherein said rotational speed is between 500 and 4000 rpm.

5. The method of claim 2 wherein said rotational speed is between 700 and 3500 rpm.

6. The method of claim 1 further comprising providing a potentiometer connected to said vibrational mill, said potentiometer being adapted to determine said vibration frequency of said vibrational mill.

7. The method of claim 6 wherein said potentiometer is adapted to communicate said vibration frequency to an operator.

8. The method of claim 1, wherein the vibration frequency is between 200 and 4500 rpm.

9. The method of claim 1, wherein the vibration frequency is between 500 and 4000 rpm.

10. The method of claim 1, wherein the vibration frequency is between 700 and 3500 rpm.

11. The method of claim 1, wherein the said means designed to regulate the vibration frequency is a potentiometer connected to the motor of the mill, which can be suitably regulated by an operator.

12. The method of 1, wherein the drug and carrier are used, optionally pre-mixed, in proportions of between 12:1 and 0.5:1 by weight.

* * * * *

UNITED STATES PATENT AND TRADEMARK OFFICE
CERTIFICATE OF CORRECTION

| | | |
|---|---|---|
| PATENT NO. | : 7,793,871 B2 | |
| APPLICATION NO. | : 12/146297 | |
| DATED | : September 14, 2010 | |
| INVENTOR(S) | : Dobetti et al. | |

It is certified that error appears in the above-identified patent and that said Letters Patent is hereby corrected as shown below:

| COLUMN | LINE | ERROR |
|---|---|---|
| 7 | 16 | after "method of claim 1" insert --,-- |
| (Claim 6, | line 1) | |

Signed and Sealed this
Eighteenth Day of January, 2011

David J. Kappos
*Director of the United States Patent and Trademark Office*